United States Patent [19]

Ellis et al.

[11] 4,091,833
[45] May 30, 1978

[54] DEVICE FOR DETECTING PREDETERMINED FOAMING CONDITIONS IN FLUIDS

[76] Inventors: Christopher Ian Arthur Ellis, Copley 'B', Manor Road, Thornton Hough, Wirral, Merseyside; Edward Leonard Naylor, 9 St. David Road, Birkenhead, Merseyside, both of England

[21] Appl. No.: 759,849

[22] Filed: Jan. 17, 1977

[51] Int. Cl.² ............................................ G05D 11/08
[52] U.S. Cl. .................................. 137/93; 134/57 R; 331/65; 361/178
[58] Field of Search ............. 134/57 R, 57 D; 137/93; 331/65; 361/178

[56] References Cited

U.S. PATENT DOCUMENTS

| | | | |
|---|---|---|---|
| 2,490,634 | 12/1949 | Keene | 134/57 D UX |
| 3,397,715 | 8/1968 | Fathauer | 361/178 X |
| 3,483,437 | 12/1969 | Coyne | 331/65 X |
| 3,796,925 | 3/1974 | Breeding | 134/57 D X |

Primary Examiner—Robert G. Nilson

Attorney, Agent, or Firm—Diller, Brown, Ramik & Wight

[57] ABSTRACT

A first inductive coil in the form of a bifilar winding is wound on a ferrite ring core with the two sections of the bifilar winding connected in series, the junction of the two sections forming the center tap of the coil. A capacitor is connected across the first coil to form a parallel resonant circuit therewith. The two ends of the first coil are respectively connected to a predetermined capacitance and to an electrode adapted to form a capacitative element whose dielectric includes a fluid under test. The center tap of the first coil is connected to the output of an amplifier whose input is connected to a second, detector coil comprising a separate winding on the ferrite ring core located substantially at the mid-point between the ends of the bifilar winding. The second coil is arranged to be inductively coupled to said first coil such that the mutual inductance between the first coil and the detector coil completes a feedback loop for the amplifier. Circuit components are included for producing an output signal dependent upon an oscillatory condition of the amplifier, the latter condition being arranged to be achieved upon the occurance of a predetermined foaming condition.

8 Claims, 7 Drawing Figures

DEVICE FOR DETECTING PREDETERMINED FOAMING CONDITIONS IN FLUIDS

The present invention relates to a device for detecting a predetermined foaming condition in a fluid or emulsion.

The presence of foam in a washing machine is an indication of the detergency of the washing liquor. If too little foam is present the soiling matter will not be held in suspension and will be redeposited on the materials being washed. If too much foam is present it is not only wasteful of materials but also reduces the efficiency of the washing action by reducing to insufficient levels the mechanical interengagement between the materials being washed. It is therefore desirable to be able to monitor the foaming condition of the washing liquor so that the detergency of the liquor can be maintained at an efficient level throughout the washing process.

It has been established by the applicants that an accurate indication of the amount of foam (referred to hereinafter as the foaming condition) in a fluid or emulsion can be obtained by the technique of utilising the fluid or emulsion under test as the dielectric of a capacitor and comparing the capacity of the latter capacitor with that of a predetermined reference capacitor.

Devices are already known which utilize this latter technique to provide a control of fluid depth. For example, in U.S. Pat. No. 3,397,715 there is described such a device for regulating the level of fluids, or particulate solids within a container, the device including a probe which co-operates with a wall of the container to define a capacitor whose dielectric is formed by the contents of the container so that, when the contents are water, the overall effective dielectric constant of the region of the container between the probe and the associated container wall varies as a function of the volume, and hence the depth, of water in the container. The device of U.S. Pat. No. 3,397,715 includes a high frequency oscillator which is coupled through a transformer to a capacitance control circuit which supplies a signal for actuating a thyristor controlled dosing element.

Devices are also known which are not responsive to the change in capacitance of a capacitor due to variations in the nature of the dielectric of the capacitor but rather to a change in the capacitance arising from variations in the spacing of the capacitor plates. For example, in G. B. Pat. No. 1,169,197 (based on U.S. Pat. No. 3,483,437 there is described a device for detecting the proximity of an object or body of material which is responsive to the changing capacitance between a fixed electrode and the object or body in question. The device employs an oscillator which provides a maximum amplitude signal in the event of the absence of the object or body and a modulated, lower signal as the body or object approaches.

It is an object of the present invention to provide a device which utilizes the aforegoing general technique but which employs circuitry which is simplified compared with the known devices and which is also specially adapted for detecting and being responsive to predetermined foaming conditions.

In accordance with the present invention, there is provided a device comprising a first inductive coil in the form of a bifilar winding wound on a ferrite ring core with the two sections of the bifilar winding connected in series, the junction of the two sections forming the center tape of the coil, a capacitor connected across the first coil to form a parallel resonant circuit therewith, the two ends of the first coil being respectively connected to a predetermined capacitance and to an electrode adapted to form a capacitative element whose dielectric, when the device is in use, includes a fluid or emulsion under test, and the center tap of the first coil being connected to the output of an amplifier whose input is connected to a second, detector coil comprising a separate winding on said core located substantially at the mid-point between the ends of the bifilar winding and inductively coupled to said first coil whereby the mutual inductance between the first coil and the detector coil completes a feedback loop for the amplifier, and circuit means for producing an output signal dependent upon an oscillatory condition of the amplifier.

As a result of the construction of the inductive coil and detector in the aforegoing manner, when the currents in the two bifiler sections, that is in the two halves of the coil, are equal the corresponding magnetic fluxes induced in the core exactly cancel each other so that the resultant flux in the core is zero. The output of the detector coil in this condition is therefore also zero.

Preferably, the two sections of the bifilar winding are connected in a series aiding configuration.

The aforegoing system has the advantage that an output signal is obtained from the amplifer whose magnitude is directly representative of the amount of foam present in the fluid being monitored so that by comparing the amplifier output signal with a preselected proportion of a fixed reference signal one can preselect the particular foaming condition, i.e., the amount of foam present, at which the device will respond. By using the output signal of the device to actuate valves controlling the supply of detergents to the fluid being monitored, the device can therefore accurately control the foaming condition and hence the detergency of the fluid to preselected standards.

The output signal of the device, which is preferably digital, is advantageously arranged to be triggered at a predetermined voltage or current output of the amplifier, the predetermined threshold voltage or current at which the digital output signal is triggered being selected to correspond to a particular amount of foam in the fluid being monitored.

In one embodiment of the invention, the electrode is adapted to be mounted on or in one wall of a fluid chamber, for example of a washing machine, said one wall being made of an electrically insulating material, an opposite wall of the fluid chamber made of conductive material forming a second electrode of said capacitative element. Alternatively, the first mentioned electrode of the capacitative element is inserted into a fluid chamber, one conductive wall of the chamber forming the other electrode of the capacitative element. In a further embodiment, the fluid or emulsion is contained within a vessel and the first mentioned electrode is located within the vessel, a second plate also located within the vessel forming the other electrode of said capacitative element.

The invention is described further hereinafter, by way of example, with reference to the accompanying drawings, in which.

Figure 1:
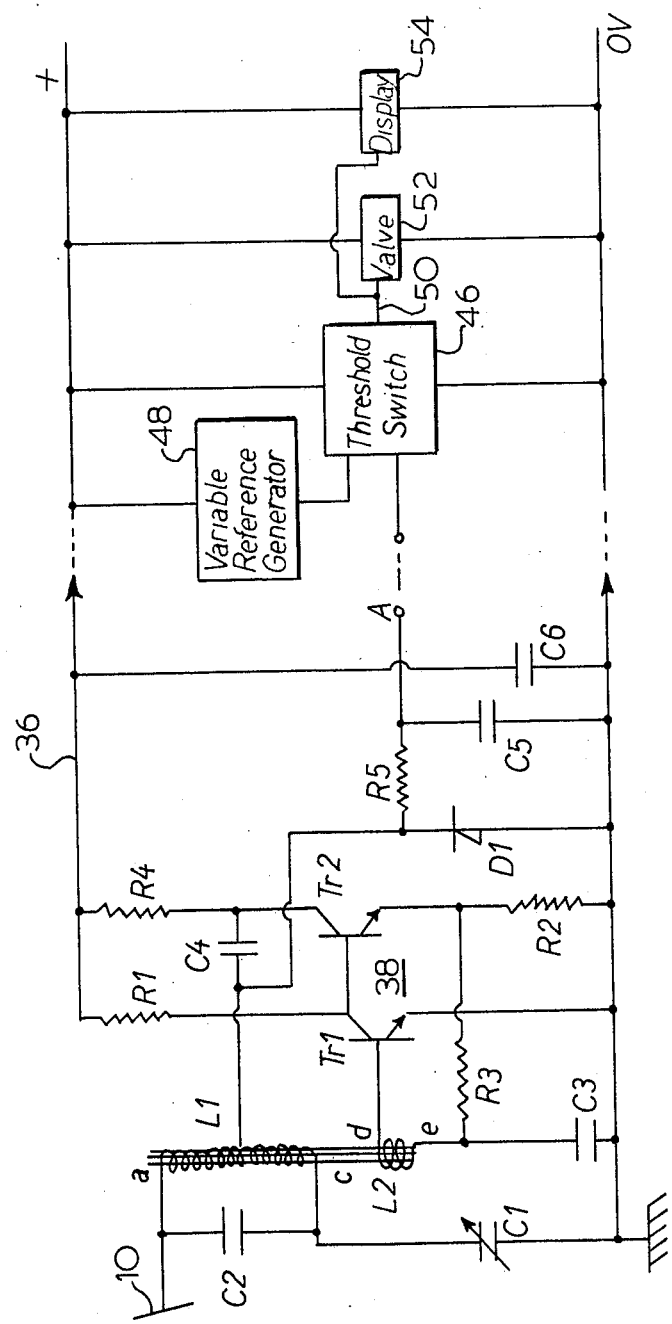
FIG. 1 is a diagrammatic illustration of one embodiment of a device in accordance with the invention.
Figure 2:
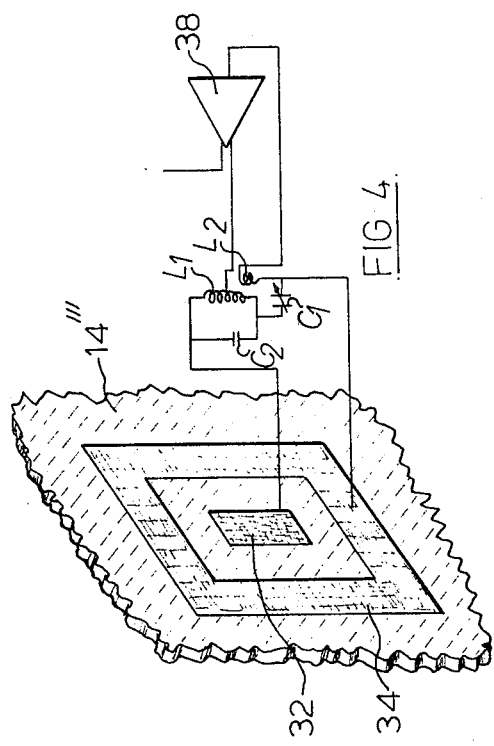
FIG. 2 is a simplified view of the device of FIG. 1, including a first detector electrode arrangement.
Figure 4:
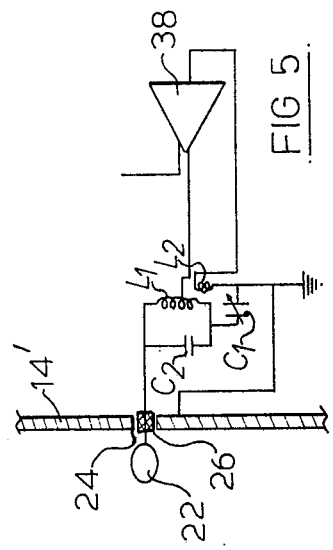
FIG. 4 is a simplified view of the device of FIG. 1, including a third detector electrode arrangement.
Figure 3:
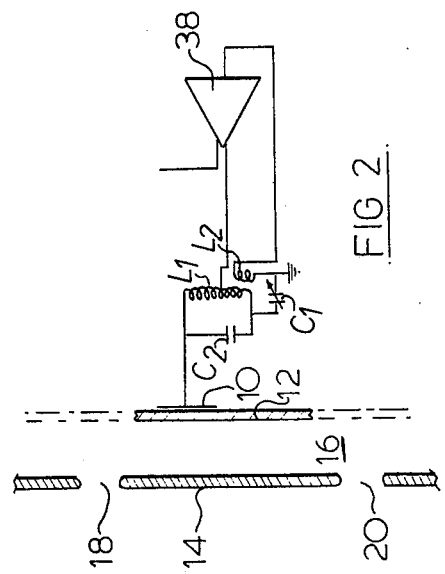
FIG. 3 is a simplified view of the device of FIG. 1, including a second detector electrode arrangement.
Figure 5:
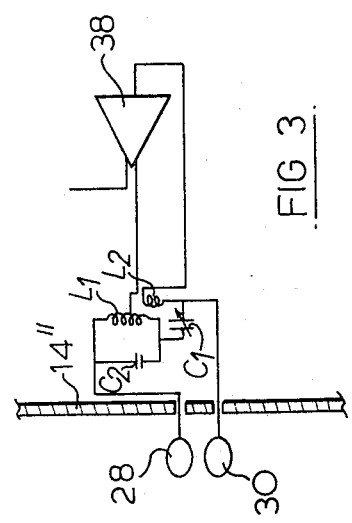
FIG. 5 is a simplified view of the device of FIG. 1, including a fourth detector electrode arrangement.
Figure 6:
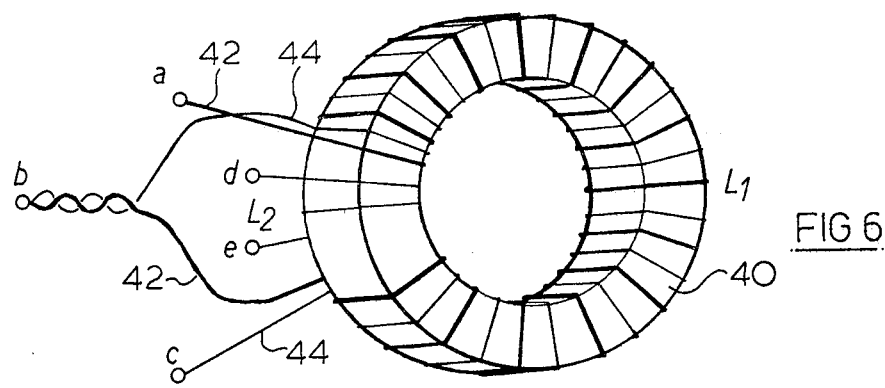
FIG. 6 is a diagrammatic perspective view, on an enlarged scale, of a multiple winding inductor for the device of FIG. 1.

With reference to FIGS. 1 and 6, the illustrated device is arranged to be responsive to the capacitance between a detector electrode 10 and a second, fixed electrode which can be earth (FIGS. 2 and 5) or a second detector electrode (FIGS. 3 and 4). For example, in the arrangement of FIG. 2, the detector electrode 10 is mounted on an outer wall 12 of a washing machine (not shown in detail). The wall 12 is made from a suitable dielectric material (for example a plastics material) and together with a metallic side or end wall 14 of the washing machine defines a fluid chamber 16. The wall 14 of the washing machine is arranged to be at earth potential and, together with the detector electrode 10, constitutes a capacitor whose capacity is hereinafter referred to a $Cx$. Fluid from the washing machine can enter and pass through the fluid chamber 16 by way of ports 18 and 20. It will be understood that the value of the capacity $Cx$ depends upon the nature of the dielectric present between the fixed wall 14 of the washing machine and the electrode 10, the dielectric being constituted in fact by the material of the wall 12 and the fluid in the chamber 16. During use of the washing machine, it will be appreciated that the latter fluid can comprise air alone, a mixture of air and liquid (foam), or water alone. The circuitry of the device described hereinafter is designed to be capable of distinguishing these conditions and various predetermined combinations thereof.

It is not necessary for a separate fluid chamber 16 to be provided on the washing machine and measurement can be made directly within the washing chamber of the machine. FIGS. 3 and 5 show such embodiments. In FIG. 5, a first detector electrode 22 extends through a bore 24 in the wall 14' of the washing machine into the fluid contained therein. The electrode 22, which is insulated from the wall 14' by an insulating bush 26, forms one electrode of the capacitor whose capacity is $Cx$, the other electrode being constituted by the metallic wall 14' which is earthed. As before, the fluid in the washing machine constitutes the dielectric of the capacitor, the value of the capacity $Cx$ depending upon the nature of the fluid.

FIG. 3 shows an embodiment employing two detector electrodes 28 and 30 extending through respective bores in the wall 14". In this case, the wall 14" is made of insulating material. The two electrodes 28 and 30 constitute the capacitor whose capacity is $Cx$ and the fluid in the washing machine between the electrodes constricts the dielectric of the capacitor.

FIG. 4 illustrates a further embodiment which employs a pair of flat detector electrodes 32 and 34 which are printed onto the surface (preferably the outer surface) of the wall 14''' of the washing machine, the wall 14''' being made of insulating material. As before, the electrodes 32,34 form the capacitor of capacity $Cx$, the nature of the fluid in the machine determining the actual value of the capacity $Cx$.

The detailed circuitry of the preferred embodiment will now be described with reference to FIG. 1, it being assumed that the detector electrode in this instance is as shown in FIG. 2 or FIG. 5 in which one electrode of the capacitor is earthed.

The capacitance $Cx$ between the electrode 10 and earth is arranged in one arm of what is effectively a capacitance bridge, the other capacitative arm of the bridge containing a variable capacitor $C_1$. The other two arms of the bridge are inductive and are formed by the two halves of a center tapped inductance $L_1$. A further capacitor $C_2$ is connected across the outer ends $a,c$ of the inductance $L_1$ to form a parallel resonant circuit with $L_1$. A second inductance $L_2$ is mounted adjacent the inductance $L_1$ so as to be inductively coupled therewith, one end $d$ of the inductance $L_2$ being connected to the base of a first NPN transistor $Tr_1$ and the other end $e$ being connected to earth via a capacitor $C_3$. The collector of transistor $Tr_1$ is connected to a positive supply line 36 via a resistor $R_1$ and to the base of a second NPN transistor $Tr_2$. The emitter of the transistor $Tr_2$ is connected to earth via a resistor $R_2$ and to the end $e$ of the inductance $L_2$ by way of a resistor $R_3$. The collector of the transistor $Tr_2$ is connected to the positive line 36 by way of a resistor $R_4$ and to the center tap $b$ of the inductance $L_1$ by way of a capacitor $C_4$. A decoupling capacitor $C_6$ is located between the supply rails.

The transistors $Tr_1$, $Tr_2$ and associated components form an amplifier (indicated generally by the reference number 38 in FIGS. 2 to 5) having a feedback loop completed by the mutual inductance between the coils $L_1$ and $L_2$ which, under certain specified conditions, can supply positive feedback to produce sustained oscillation of the amplifier at approximately the resonant frequency of the parallel circuit $L_1$, $C_2$.

The resistors $R_2$ and $R_3$ form a self-compensating d.c. bias for the amplifier, the capacitor $C_3$ providing a.c. decoupling. An additional capacitor (not shown) can optionally be included in parallel with $R_2$ for increasing the internal a.c. gain of the amplifier, rendering the circuit more responsive to very small changes in the capacitance between the electrode 10 and earth.

The construction of the inductors $L_1$, $L_2$ is critical to the operation of the device. As illustrated in FIG. 6, the inductance $L_1$ comprises a bifilar wound coil on a ferrite ring core 40, the two sections of the coil being connected in "series aiding" configuration with the junction of the two sections forming the center tap $b$. The coil $L_1$ is thus formed by winding two wires 42,44 as a parallel pair onto the core 40, the end of the wire 42 at one end of said pair forming the terminal $a$. The end of the wire 42 at the other end of the wound pair is connected to the end of the wire 44 at the first end of the wound pair to form the center tap $b$, and the end of the wire 44 at said other end of the wound pair forms the terminal $c$.

Located at the mid-region of the portion of the core 40 between said ends of the wound pair 42,44 is the detector coil $L_2$, this coil $L_2$ therefore occupying a neutral position relative to the coil $L_1$.

Thus, the bifilar nature of the windings 42,44 ensures that the points $a$ and $c$ are symmetrically located relative to point $b$ so that when the currents in the windings 42,44 are equal, the resultant magnetic flux in the core 40 is zero and no current is induced in the coil $L_2$. There is then no feedback input to the amplifier $Tr_1$, $Tr_2$ and hence no oscillation of the amplifier. This condition is met when the capacitance between the detector electrode 10 and earth is equal to the capacitance of capacitor $C_1$, the bridge then being in balance.

It will be noted from the drawings that the two halves of coil $L_1$ are wound in opposite senses relative to the center tap $b$. This has the result that, with the connections as illustrated, if the capacitance of $C_1$ should be greater than the capacitance $Cx$ between detector electrode 10 and earth, i.e., the latter capacitance falls, any resultant flux produced in the core 40 by virtue of the difference between currents in the two halves of $L_1$ induces a corresponding current in the coil $L_2$ but, since this is in anti-phase with the current in $L_1$, the feedback is negative and acts degeneratively and no oscillation of the amplifier occurs.

On the other hand, when the capacitance $Cx$ between the detector electrode 10 and earth increases so as to exceed that of capacitor $C_1$, the induced current in coil $L_2$ is in phase with that in $L_1$ and the feedback is positive and is effective to sustain continuous oscillation of the amplifier. In the latter conditions, the magnitude of the output signal of the amplifier is dependent upon the unbalance of the bridge and hence upon the amount by which the capacitance of the capacitor formed between the electrode 10 and earth exceeds the fixed capacity of $C_1$.

It will also be noted that the circuit operates equally well in the opposite mode. For example, when the connections to the coil $L_2$ are reversed, then if the capacitance $Cx$ between electrode 10 and earth is less than that of $C_1$, the feedback will be positive and the circuit will oscillate. An increased capacitance $Cx$ at the electrode 10 then produces negative feedback which inhibits the oscillations.

Figure 7:
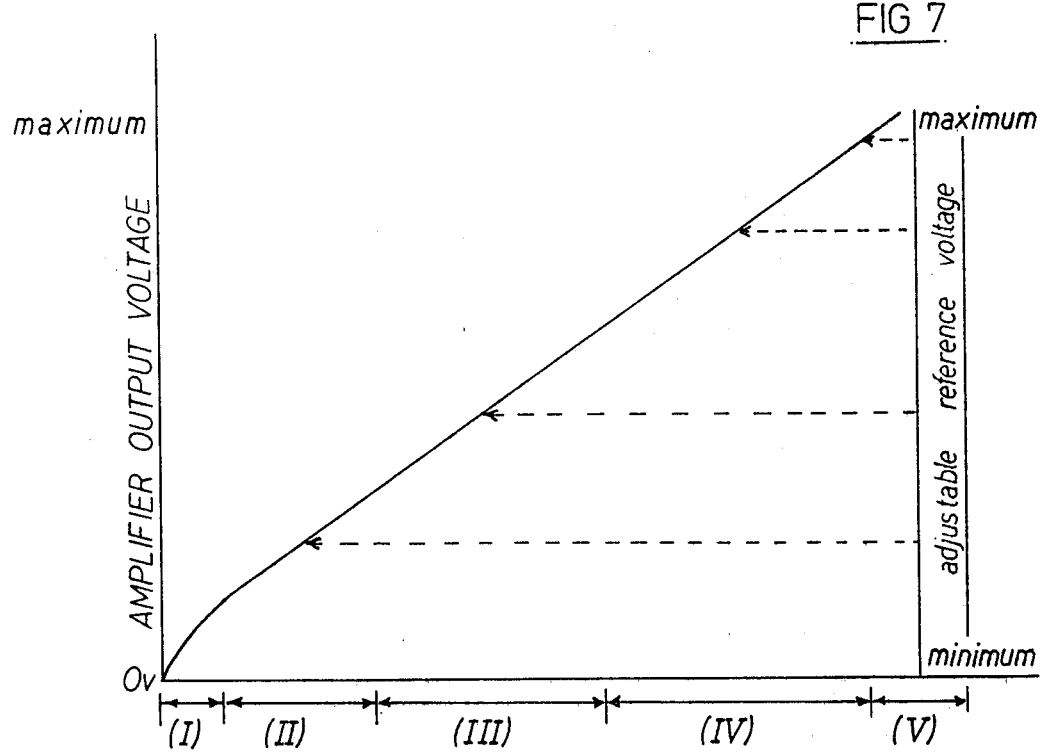
FIG. 7 is a graph illustrating the output voltage of the amplifier in the device of FIG. 1 with change in the foaming condition of the fluid or emulsion being monitored.

The circuit includes additional components for providing an output signal, and preferably also visual indication, when the front part of the circuit, so far described, is producing oscillations in excess of a predetermined threshold magnitude. With reference to FIG. 1, a D.C. output A proportional to the voltage output of the amplifier 38 is taken from the junction of the capacitor $C_4$ and the coil $L_1$ via a resistor $R_5$, rectification and smoothing being achieved by a diode $D_1$ and capacitor $C_5$, respectively, It has been established by the Applicants that a definite relationship exists between the output of the amplifier 38 and the nature of the environment (amount of foam) intermediate the electrodes of the detection capacitor. If, for example, the circuit constants are so proportioned that the amplifier output is zero when the detector electrode 10 is in dry air, a progressively increasing output A can be observed as the nature of the environment (amount of foam) is changed. The graph of FIG. 7 illustrates the effect referred to. In this graph, the Y ordinate represents output voltage A of the amplifier and the X abscissa represents the relative amounts of air and liquid in the fluid adjacent the electrode 10, portion (i) being pure air; portion (ii) being water vapor, oil mist and the like; portion (iii) being emulsions such as formed by oils and greases in water; portion (iv) being foam caused for example by detergents and soaps in water; and portion (v) being pure liguid such as pure water.

The circuit further includes a threshold switch 46 which receives both the amplifier output signal A and a preselectable reference voltage from a suitable generator 48, the switch being adapted to provide an output on a line 50 upon equivalence of the signals at its two inputs. As indicated at the right hand side of FIG. 7, by selecting the magnitude of the reference voltage from the generator 48 with which the output A of the amplifier $TR_1$, $Tr_2$ is compared, the output on the line 50 can be preselected to appear only when a specified foaming condition is present between the electrodes of the detector capacitor. For example, if a fixed stable reference voltage is provided in the generator 48, selected portions of this reference can be compared with the output A of the amplifier in the switch 46 so that the latter switch operates at specific output levels A indicative of the desired foaming condition.

The digital output on the line 50 can be used in a conventional manner to actuate or de-actuate one or more relays 52 and, if desired, a visual indication device 54 such as a lamp or L.E.D. The relay or relays 52 can be used in a conventional manner to operate suitable valves for the admission of detergents until such time as a preselected foaming condition has been achieved, at which time the circuit automatically closes the valves. Should the foaming condition fall below the preselected standard, the circuit controls the admission of further supplies of detergent to re-establish the foam condition to the preselected standard.

The aforegoing system may be used to identify particular environments and to operate suitable trigger circuits to provide outputs for measurement or control purposes, or may be used to indicate and operate upon a change of state from one set of conditions to another, for example from state (iii) to state (iv) in FIG. 7.

Although only one threshold switch or comparator 46 is illustrated in FIG. 1, several such switches 46 could be provided in some embodiments each of which switches is responsive to different predetermined threshold levels and hence to different predetermined foaming conditions.

For convenience, the circuit parts 46, 48, 50, 52 and 54 of the embodiment of FIG. 1 can conveniently be mounted at a location remote from the electrode 10 whereas the other circuit components associated with the bridge circuit and the amplifier can be mounted in a unit adjacent or with the detector electrode 10.

Although described above as being proportional to the voltage output of the amplifier $Tr_1$, $Tr_2$, the output A could equally well be proportional to the current output of the amplifier.

In order to prevent hunting following the generation of a digital output pulse on the line 50, additional circuit means (not shown) are preferably provided to inhibit the generation of a further digital output pulse until a predetermined period has elapsed.

The embodiments of the invention shown in the drawings have all been described above in conjunction with washing machines. However, the invention is not limited to the detection and indication of foam in washing machines and can be used to detect and indicate the proportions of liquid and gas in any foam or emulsion.

We claim:
1. A device responsive to a foaming condition in a fluid comprising:
   a first inductive coil comprising a bifilar winding wound on a ferrite ring core with the two sections of the bifilar winding connected in series, the junction of said two sections forming the center tap of the coil;
   capacitor means connected across the first coil to form a parallel resonant circuit therewith;

first detector electrode means connected to one end of said first coil and adapted in use of the device to form one electrode of a capacitative element whose dielectric includes the fluid under test;

second detector electrode means adapted to form the other electrode of said capacitative element;

second capacitor means connected between the other end of said first coil and said second detector electrode means;

amplifier means having an input and an output, said amplifer output being coupled to said center tap of said first inductive coil;

a second, detector coil comprising a separate winding on said core located substantially at the mid-point between the ends of the bifilar winding and connected to the input of said amplifier, said second, detector coil being inductively coupled to said first coil whereby the mutual inductance between said first and second coil completes a feedback loop for said amplifier means; and circuit means for producing an output signal dependent upon an oscillatory condition of said amplifier means.

2. A device according to claim 1 in which said circuit means include;

means for producing a D.C. signal proportional to the magnitude of the output of said amplifier means;

variable reference generating means for providing a reference signal of preselectable magnitude;

threshold switch means having first and second inputs which receive said D.C. signal and said reference signal, respectively, the threshold switch means being adapted to provide an output signal upon the occurrence of equivalence of said signals at its inputs; and valve means operable in response to said output signal of the threshold switch means for supplying additional quantities of detergent to increase the foaming condition of said fluid.

3. A device responsive to a predetermined foaming condition in a fluid comprising:

a first inductive coil comprising a bifilar winding wound on a ferrite ring core with the two sections of the bifilar winding connected in series, the juncton of said two sections forming the center tap of the coil;

capacitor means connected across the first coil to form a parallel resonant circuit therewith;

first detector electrode means connected to one end of said first coil and adapted in use of the device to form one electrode of a capacitative element whose dielectric includes the fluid under test;

second detector electrode means adapted to form the other electrode of said capacitative element;

second capacitor means connected between the other end of said first coil and said second detector electrode means;

amplifier means having an input and an output, said amplifier output being coupled to said center tap of said first inductive coil;

a second, detector coil comprising a separate winding on said core located substantially at the mid-point between the ends of the bifilar winding and connected to the input of said amplifier, said second, detector coil being inductively coupled to said first coil whereby the mutual inductance between said first and second coils completes a feedback loop for said amplifier means; and circuit means for producing an output signal dependent upon the output of said amplifier means reducing a predetermined magnitude.

4. In an automatic washing machine having a washing chamber, a device responsive to a predetermined foaming condition of the washing fluid of the machine comprising:

a first inductive coil comprising a bifilar winding wound on a ferrite ring core with the two sections of the bifilar winding connected in series, the junction of said two sections forming the center tap of the coil;

capacitor means connected across the first coil to form a parallel circuit therewith;

first detector electrode means mounted adjacent the washing chamber of the machine and connected to one end of said first coil and adapted in use of the device to form one electrode of a capacitative element whose dielectric includes the machine washing fluid under test;

second detector electrode means adapted to form the other electrode of said capacitative element;

second capacitor means connected between the other end of said first coil and said second detector electrode means;

amplifier means having an input and an output, said amplifier output being coupled to said center tap of said first inductive coil;

a second, detector coil comprising a separate winding on said core located substantially at the mid-point between the ends of the bifilar winding and connected to the input of said amplifier, said second, detector coil being inductively coupled to said first coil whereby the mutual inductance between said first and second coils completes a feedback loop for said amplifier means; and circuit means for producing an output signal dependent upon an oscillatory condition of said amplifier means.

5. A washing machine according to claim 4 in which said first detector electrode means is mounted on one upright wall of the washing chamber of the machine, said one wall being made of an electrically insulating material, and in which said second detector electrode means is formed by an opposite wall of the washing chamber made of electrically conductive material.

6. A washing machine according to claim 4, in which said first detector electrode means of said capacitative element lies within the washing chamber of the machine, and in which the second detector electrode means of the capacitative element is formed by an electrically conductive wall of said washing chamber.

7. A washing machine according to claim 4 in which both said first and second detector electrode means of the capacitative element are located within the washing chamber of the machine.

8. A washing machine according to claim 4 in which both said first and second detector means of the capacitative element are in the form of electrically conducting plates mounted on an electrically insulating wall of said washing chamber.

* * * * *

UNITED STATES PATENT AND TRADEMARK OFFICE
CERTIFICATE OF CORRECTION

PATENT NO. : 4,091,833
DATED : May 30, 1978
INVENTOR(S) : Christopher Ian Arthur Ellis et al.

It is certified that error appears in the above-identified patent and that said Letters Patent is hereby corrected as shown below:

On the title page, Insert the assignee data:

-- (73) Assignee: Malcom-Ellis (Liverpool) Limited --.

Signed and Sealed this

Ninth Day of November 1982

[SEAL]

Attest:

GERALD J. MOSSINGHOFF

Attesting Officer

Commissioner of Patents and Trademarks